United States Patent
Miyata et al.

(10) Patent No.: US 9,272,122 B2
(45) Date of Patent: *Mar. 1, 2016

(54) SHAFT AND GUIDEWIRE EMPLOYING THE SAME

(71) Applicant: ASAHI INTECC CO., LTD., Nagoya-shi, Aichi (JP)

(72) Inventors: Naohiko Miyata, Nagoya (JP); Muneya Furukawa, Seto (JP); Kenichi Matsuo, Izumiotsu (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,229

(22) Filed: Jun. 26, 2014

(65) Prior Publication Data

US 2015/0094692 A1     Apr. 2, 2015

(30) Foreign Application Priority Data

Oct. 2, 2013  (JP) .................................. 2013-207156

(51) Int. Cl.
- *A61B 5/00* (2006.01)
- *A61M 25/00* (2006.01)
- *A61M 25/09* (2006.01)
- *B21F 7/00* (2006.01)

(52) U.S. Cl.
CPC ......... *A61M 25/09016* (2013.01); *A61M 25/09* (2013.01); *A61M 2025/09075* (2013.01); *A61M 2025/09083* (2013.01); *A61M 2025/09108* (2013.01); *A61M 2025/09133* (2013.01); *A61M 2025/09191* (2013.01); *B21F 7/00* (2013.01)

(58) Field of Classification Search
CPC ............ A61M 25/09; A61M 2025/09; A61M 2025/09116; A61M 2025/09191; A61M 25/09016
USPC ......................................................... 600/585
See application file for complete search history.

(56) References Cited

U.S. PATENT DOCUMENTS

| | | | |
|---|---|---|---|
| 5,299,580 A | 4/1994 | Atkinson et al. |
| 5,313,967 A | 5/1994 | Lieber et al. |
| 6,059,771 A | 5/2000 | Balbierz et al. |
| 8,113,916 B2 | 2/2012 | Miller et al. |
| 2002/0043118 A1 | 4/2002 | Claude |
| 2004/0142643 A1 | 7/2004 | Miller et al. |

(Continued)

FOREIGN PATENT DOCUMENTS

| | | |
|---|---|---|
| EP | 0 826 389 A2 | 3/1998 |
| EP | 2 163 276 A1 | 3/2010 |

(Continued)

OTHER PUBLICATIONS

Sep. 11, 2014 Search Report issued in European Patent Application No. 14173742.9.

(Continued)

*Primary Examiner* — Brian Szmal
(74) *Attorney, Agent, or Firm* — Oliff PLC (57) ABSTRACT

A shaft suppresses a permanent set, or plastic deformation, even when inserted into an extremely winding blood vessel. A guidewire incorporates the above shaft. The shaft is twisted along its longitudinal axis and has a cross section forming a substantially rectangular shape extending in a first direction perpendicular to the longitudinal axis. The cross section has at least one arcuate recess.

11 Claims, 8 Drawing Sheets

(56) References Cited

U.S. PATENT DOCUMENTS

| 2004/0215109 | A1 | 10/2004 | Pingleton et al. |
| 2013/0304108 | A1 | 11/2013 | Weber et al. |
| 2014/0103273 | A1 | 4/2014 | Nakajima et al. |
| 2015/0094691 | A1 | 4/2015 | Miyata et al. |
| 2015/0094692 | A1 | 4/2015 | Miyata et al. |

FOREIGN PATENT DOCUMENTS

| JP | 101216236 | | 8/1998 |
| JP | 2008-155054 | A | 7/2008 |
| JP | 2011-125556 | A | 6/2011 |
| JP | A-2012-070906 | | 4/2012 |
| JP | 2013-085781 | A | 5/2013 |
| JP | 2015-70895 | A | 4/2015 |
| JP | 2015-70896 | A | 4/2015 |
| WO | WO 2012/172881 | A1 | 12/2012 |

OTHER PUBLICATIONS

Mar. 6, 2015 Search Report issued in European Search Report Application No. 14173746.0.
Mar. 12, 2015 Search Report issued in European Search Report Application No. 14173744.5.
U.S. Appl. No. 14/310,437, filed Jun. 20, 2014.
U.S. Appl. No. 14/315,990, filed Jun. 26, 2014.
Jul. 29, 2015 Office Action issued in U.S. Appl. No. 14/315,990.
Nov. 9, 2015 Office Action issued in Japanese Patent Application No. 2013-252887.
Nov. 17, 2015 Office Action issued in Japanese Patent Application No. 2013-207156.
Nov. 17, 2015 Written Directive in Japanese Patent Application No. 2013-207156.
Nov. 17, 2015 Office Action issued in Japanese Patent Application No. 2013-207162.
Nov. 17, 2015 Written Directive in Japanese Patent Application No. 2013-207162.

SHAFT AND GUIDEWIRE EMPLOYING THE SAME

CROSS-REFERENCE TO RELATED APPLICATION

This application claims priority to Japanese Application No. 2013-207156 which was filed on Oct. 2, 2013, the entire contents of which is hereby incorporated by reference.

BACKGROUND

The disclosed embodiments relate to a medical device. Specifically, the disclosed embodiments relate to a shaft employed on a medical apparatus inserted into a body cavity for the purpose of treatment or an exam, and a guidewire employing the shaft.

Conventionally, various medical apparatuses inserted into a tubular organ and body tissue such as a blood vessel, a digestive tract and ureter have been proposed for the purpose of treatment or examination.

For example, U.S. Patent Application Publication No. 2004/0215109 discloses a guidewire including a shaft twisted around a long axis.

SUMMARY

When inserting a conventionally known guidewire along an inverted U-shaped path from the lower extremity vasculature of the right leg into the lower extremity vasculature of the left leg by, for example, the Cross-Over method, in such an extremely winding lower extremity vasculature, a shaft of the guidewire may bend excessively due to a load applied thereto when coming into contact with a blood vessel wall or the like. Accordingly, a permanent set (plastic deformation) may occur in the shaft which may possibly interfere with subsequent operation.

The disclosed embodiments have been devised in view of such circumstances, and it is an object of the present invention to provide a shaft capable of suppressing a permanent set even when it is inserted into an extremely winding blood vessel, and a guidewire employing the shaft.

In order to solve the above-described problem, a shaft according to aspects of the present invention and a guidewire employing the shaft have features described below.

A shaft according to a first aspect of the present invention is a shaft twisted along its longitudinal axis, having a cross section formed in a substantially rectangular shape extending in a first direction perpendicular to the longitudinal axis, in which the cross section has at least one arcuate recess.

A second aspect of the present invention is the shaft according to the first aspect having a first recess and a second recess formed on a first pair of sides opposite to each other among sides forming the cross section.

A third aspect of the present invention is the shaft according to the first aspect or the second aspect having a first arcuate projection and a second arcuate projection on a second pair of sides opposite to each other.

A fourth aspect of the present invention is the shaft according to the third aspect where a radius of curvature of the first projection and the second projection is smaller than a radius of curvature of a virtual circle having a diameter equivalent to a length of the cross section in the first direction.

A fifth aspect of the present invention is a guidewire including a core shaft and a coiled body covering a distal portion of the core shaft, in which a proximal end of the core shaft is the shaft according to any one of the first to fourth aspects.

A sixth aspect of the present invention is the guidewire according to the fifth aspect having the coiled body composed of a plurality of helically wound strands, each strand being made of a plurality of wires.

The shaft of the first aspect has a cross section with an arcuate recess. In this manner, in the shaft having a cross section with an arcuate recess, compared to a configuration without such a recess (for example, a shaft having a cross-sectional rectangular shape), an area moment of inertia is lowered.

Therefore, when the shaft enters along a path winding in an inverted U-shape from the lower extremity vasculature of the right leg into the lower extremity vasculature of the left leg by, for example, the Cross-Over method, a permanent set (plastic deformation) tends not to occur in the shaft even when subjected to a load caused by contact with a blood vessel wall or the like that bends the shaft excessively. Thus, there is no possible trouble in subsequent operation, thereby making it possible to use the shaft continuously.

In the shaft of the second aspect, arcuate recesses are formed on a first pair of sides opposite to each other among sides forming a cross section. Thereby, compared to a configuration without such recesses (a shaft having a cross-sectional rectangular shape), an area moment of inertia is still further lowered. Therefore, for example, within a blood vessel of a lower extremity region that is extremely winding in an inverted U-shape, a permanent set is further prevented in the shaft even when subjected to a load caused by contact with a blood vessel wall or the like to bend the shaft excessively. Thus, there is no possible trouble in subsequent operation, thereby making it possible to use the shaft continuously.

The shaft of the third aspect has arcuate projections on a second pair of sides opposite to each other. Top parts of the projections come into contact with a blood vessel wall. That is, compared to a configuration without such projections (a configuration having a cross-sectional rectangular shape whose four corners are in contact with a blood vessel wall), contact parts with a blood vessel wall are reduced as much as possible in the shaft according to the above aspect, while a load applied to the blood vessel wall in contact also gets smaller.

Accordingly, operation resistance of the shaft as it is pushed and pulled is reduced so that torque transmission characteristics are enhanced, resulting in improved operability. That is, even in a case where the above shaft is inserted along an inverted U-shaped path from the lower extremity vasculature of the right leg into the lower extremity vasculature of the left leg by, for example, the Cross-Over method, when passing through the top of the path, sliding against the blood vessel wall and the like do not cause movement of the shaft to be suppressed, so that a distal portion of the shaft is allowed to be inserted deeply and smoothly into the path. In addition, it is possible to reduce damage of a blood vessel.

In the shaft of the fourth aspect, the radius of curvature of a projection is smaller than the radius of curvature of a virtual circle whose diameter is equivalent to a length of the cross-section in the first direction. Such a shaft has a cross section in a tapered shape, and has two tops of respective projections in contact with a blood vessel wall. Therefore, compared to a configuration without such projections (a configuration having a cross-sectional rectangular shape whose four corners are in contact with a blood vessel wall), contact areas (contact parts) with a blood vessel wall are reduced.

Accordingly, when the above shaft rotates and enters the inside of a blood vessel, operation resistance of the shaft as it is pushed and pulled is reduced so that sufficient torque transmission characteristics are obtained, resulting in further improved operability. Furthermore, it is possible to reduce damage of a blood vessel as much as possible.

The guidewire of the fifth aspect includes a core shaft and a coiled body covering a distal portion of the core shaft, in which a proximal end of the core shaft is the shaft according to any one of the first to fourth aspects. Therefore, it is possible to obtain the above-described effect according to the first to fourth aspects. That is, in the case of the guidewire entering along an extremely winding path in an inverted U-shape, a permanent set tends not to occur in the shaft even when subjected to a load caused by contact with a blood vessel wall or the like to bend the guidewire excessively.

Further, it is possible to insert a distal portion of the guidewire into an extremely winding blood vessel in an inverted U-shape deeply and smoothly. Moreover, operation resistance of the guidewire as it is pushed and pulled is further reduced, while making it possible to reduce damage of a blood vessel effectively.

The guidewire of the sixth aspect includes a coiled body composed of a plurality of helically wound strands, each strand being made of a plurality of wires. Thereby, compared to a guidewire including a coiled body composed of, for example, a single wire having an external diameter nearly equal to that of the guidewire of the sixth aspect, flexibility of the coiled body is improved, and it is possible to secure sufficient torque transmission characteristics. Further, breaking strength against twisting is improved, so that safety of the guidewire is also enhanced.

DETAILED DESCRIPTION OF EMBODIMENTS

Description will be given for a shaft according to the disclosed embodiments shown in the drawings.

Figure 1:
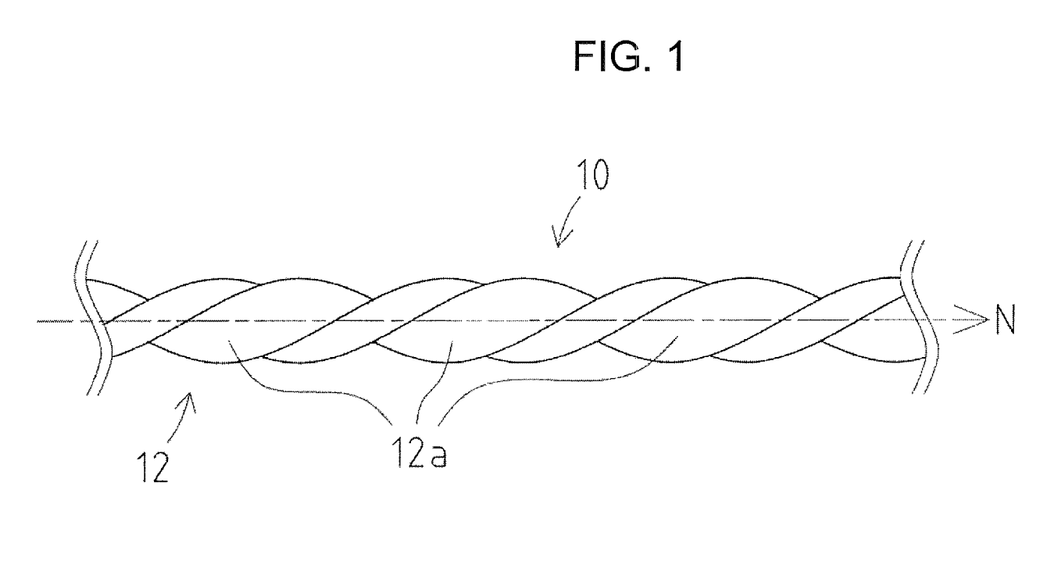
FIG. 1 is a general view showing a shaft.

FIG. 1 is a general view showing an exemplary embodiment of a shaft of the present invention. Note that, in this figure, a length direction of the shaft is shortened to be schematically illustrated in whole in order to facilitate understanding. Thus, dimensions shown do not necessarily reflect actual dimensions.

As shown in FIG. 1, a shaft 10 is formed as a rod-like body in an elongated shape. The shaft 10 can be formed using materials such as, but not limited to, for example, stainless steel (SUS304), a super elastic alloy such as an Ni—Ti alloy, and a piano wire.

The shaft 10 is twisted in a predetermined direction along its longitudinal axis N, and has a helically shaped portion 12. Additionally, the shaft 10 is provided with a plurality of grooves 12a at regular intervals along the longitudinal axis N. Thereby, for example, when inserting the shaft 10 into a blood vessel, the plurality of grooves 12a leads to reduction of contact areas with a blood vessel wall.

Further, the shaft 10 has the helically shaped portion 12, and when a proximal end of the shaft 10 is rotated, such rotation is easily transmitted to a distal end of the shaft 10. That is, torque transmission characteristics are enhanced, resulting in improved operability.

In FIG. 1, a direction of helix of the helically shaped portion 12 is counterclockwise along the longitudinal axis N of the shaft 10. However, the direction of helix of the helically shaped portion 12 is not limited thereto, and may be clockwise along the longitudinal direction N of the shaft 10.

Figure 2:
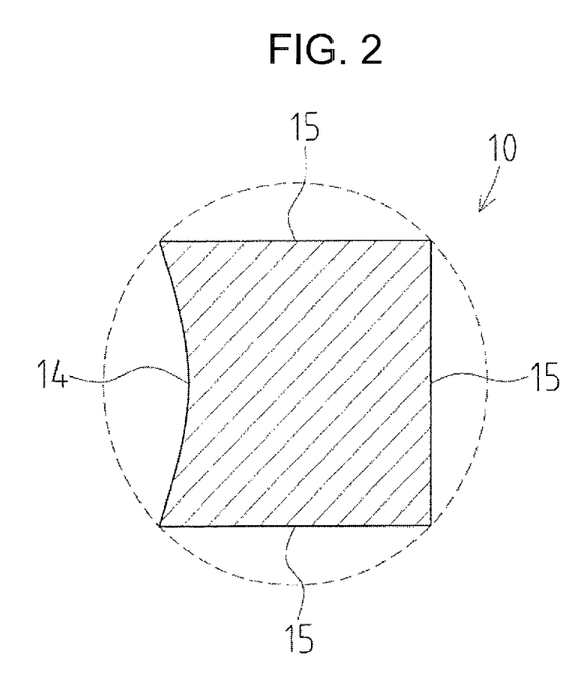
FIG. 2 is a cross-sectional view showing a shaft according to an exemplary embodiment.

As shown in FIG. 2, the shaft 10 has a cross section in a substantially rectangular shape extending in a direction perpendicular to the longitudinal axis N (hereinafter, simply referred to as a cross section). Further, the cross section has a recess 14 recessed arcuately (i.e., an arcuate recess). In the present embodiment, the recess 14 is provided only on one side among four sides forming the cross section. Moreover, the other three sides are linear portions 15 formed linearly.

In the present embodiment in which the recess 14 is provided on one side among sides forming a cross section, compared to a configuration without any such the recess 14 (a shaft having a cross-sectional rectangular shape), an area moment of inertia of the shaft 10 is lowered. Thereby, when allowing the shaft to enter along a path winding in an inverted U-shape from the lower extremity vasculature of the right leg into the lower extremity vasculature of the left leg by, for example, the Cross-Over method, a permanent set may be prevented in the shaft even when the shaft bends excessively when subjected to a load caused by contact with a blood vessel wall or the like. Therefore, there is no possible trouble in subsequent operation, thereby making it possible to use the shaft 10 continuously.

It is possible to fabricate the shaft 10 according to a method described below. First, a columnar metallic body is prepared to be rolled out from a predetermined direction. Thereafter, a rotary device is prepared, capable of applying rotary motion to a circumference of the metallic body having one end fixed, followed by rotation around a longitudinal axis of the metallic body from the other end.

Further, a distal end of the metallic body is fixed to one end of the rotary device while a proximal end of the metallic body is fixed to the other end of the rotary device. Thereafter, rotary motion is applied from the other end of the rotary device, so that the metallic body is twisted from the proximal end. Thereby, the shaft 10 is formed, including the helically shaped portion 12 twisted evenly along the longitudinal axis N.

The helically shaped portion 12 is twisted by the rotary device. Thereafter a heat treatment process mitigates the stress applied by the twisting to stabilize the final shape. A method of forming the helically shaped portion 12 is not limited to the above-described method, and the shaft 10 may be fabricated by the other known method adopted appropriately.

Figure 3:
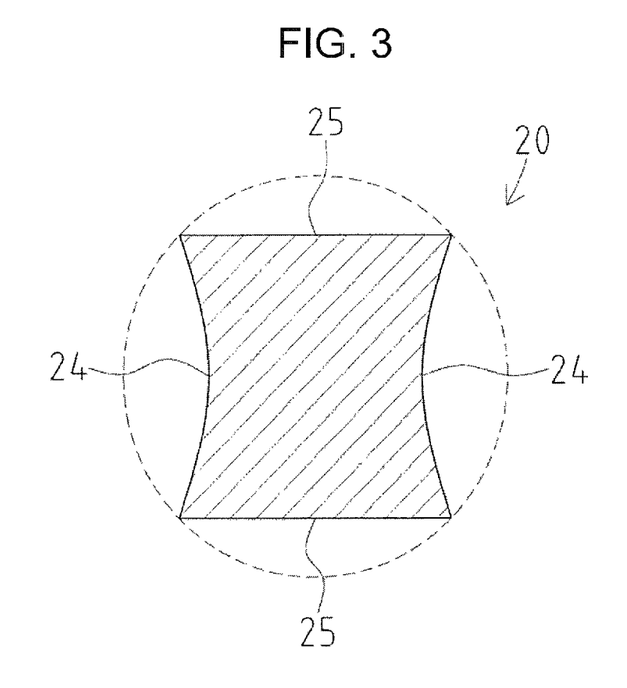
FIG. 3 is a cross-sectional view showing a shaft according to an exemplary embodiment.

FIG. 3 is a cross-sectional view according to an exemplary embodiment. Note that, in this figure, a cross section of the shaft is schematically illustrated for understanding. Thus the dimensions shown do not necessary reflect actual dimensions.

In the shaft 10 described above, the arcuate recess 14 is provided only on one side among sides forming a cross section, and linear portions 15 are provided on the other sides. Whereas, in a shaft 20, arcuate recesses 24 are formed on a first pair of sides opposite to each other. On sides except those having the pair of the recesses 24, linear portions 25 are provided, respectively.

Thereby, compared to not only a configuration without a recess (a shaft having a cross-sectional rectangular shape) but also to a configuration having only the recess 14 provided on one side among sides forming a cross section, an area moment of inertia is still further lowered.

Therefore, for example, within a blood vessel of a lower extremity region extremely winding in an inverted U-shape, a permanent set may be further prevented in the shaft 20 even when the shaft is subjected to a load caused by contact with a blood vessel wall or the like so that it is bent excessively. Thus, there is no possible trouble in subsequent operation, thereby making it easy to use the shaft 20 continuously.

Figure 4:
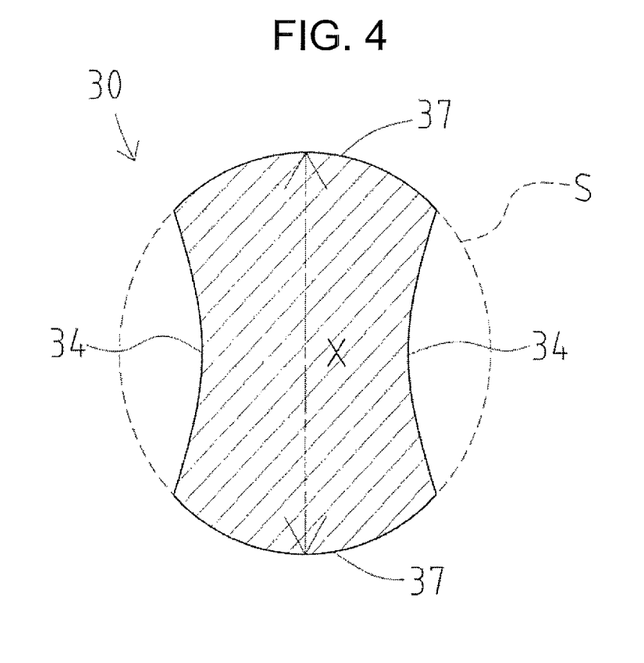
FIG. 4 is a cross-sectional view showing a shaft according to an exemplary embodiment.

FIG. 4 is a cross-sectional view according to an exemplary embodiment. Note that, in this figure, a cross section of the shaft is schematically illustrated for understanding. Thus the dimensions shown do not necessarily reflect actual dimensions.

In the shaft 20 described above, the arcuate recesses 24 are formed on a first pair of sides opposite to each other, and the linear portions 25 are provided respectively on sides except those having the pair of the recesses 24. Whereas, in a shaft 30, on a second part of sides opposite to each other, projections 37 projected arcuately (i.e., arcuate projections) are provided, respectively. Here, the radius of curvature of each projection 37 is set so as to be approximately the same as the radius of curvature of a virtual circle S having a diameter equivalent to a length X of the cross section.

Thereby, when inserting the shaft 30 into a blood vessel, only the top parts of the projections 37 provided on the second pair of sides come into contact with a blood vessel wall. Thus, as compared to a configuration without such the projections 37 (for example, a configuration having a cross-sectional rectangular shape whose four corners are in contact with a blood vessel wall), contact parts with a blood vessel wall are reduced, while a load applied to the blood vessel wall in contact is also smaller.

Therefore, when the shaft 30 rotates and enters the inside of a blood vessel, operation resistance against a blood vessel wall is reduced. Accordingly, operation resistance of the shaft 30 as it is pushed and pulled is reduced so that sufficient torque transmission characteristics are obtained, resulting in enhanced operability.

Moreover, even in a case where the above shaft 30 is inserted along an inverted U-shaped path from the lower extremity vasculature of the right leg into the lower extremity vasculature of the left leg by, for example, the Cross-Over method, when passing through the top of the path, sliding against the blood vessel wall and the like do not suppress movement of the shaft 30. This allows a distal portion of the shaft to be inserted deeply and smoothly into the path. In addition, it is possible to reduce damage of a blood vessel.

Figure 5:
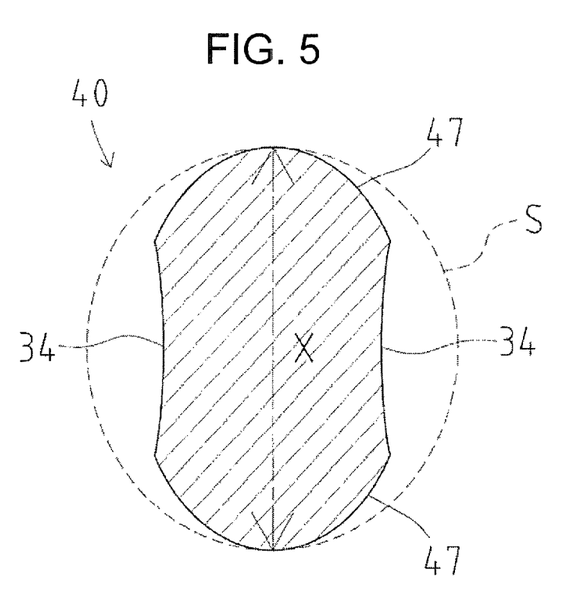
FIG. 5 is a cross-sectional view showing a shaft according to an exemplary embodiment.

FIG. 5 is a cross-sectional view according to an exemplary embodiment. As before, a cross section of the shaft is schematically illustrated. Thus, the dimensions shown do not necessarily reflect actual dimensions.

In the shaft 30, the arcuate projections 37 are provided respectively on a second pair of sides opposite to each other, and the radius of curvature of these projections 37 is set so as to be approximately the same as the radius of curvature of the virtual circle S having a diameter equivalent to the length X of the cross section. Whereas, in a cross section forming a shaft 40, the radius of curvature of a pair of projections 47 is smaller than the radius of curvature of the virtual circle S having a diameter equivalent to the length X of the cross section.

Such a shaft 40 has a cross section in a tapered shape, and has two tops of respective projections 47 in contact with a blood vessel wall. Therefore, compared to not only a configuration without a projection (a configuration having a cross-sectional rectangular shape whose four corners are in contact with a blood vessel wall) but also the configuration in which a projection is provided having the radius of curvature approximately the same as the radius of curvature of the virtual circle S, contact areas (contact parts) with a blood vessel wall are further reduced.

Accordingly, when the shaft 40 rotates and enters the inside of a blood vessel, operation resistance of the shaft 40 as it is pushed and pulled is reduced so that sufficient torque transmission characteristics are secured, resulting in still further enhanced operability. Furthermore, it is possible to reduce damage of a blood vessel.

Figure 6:
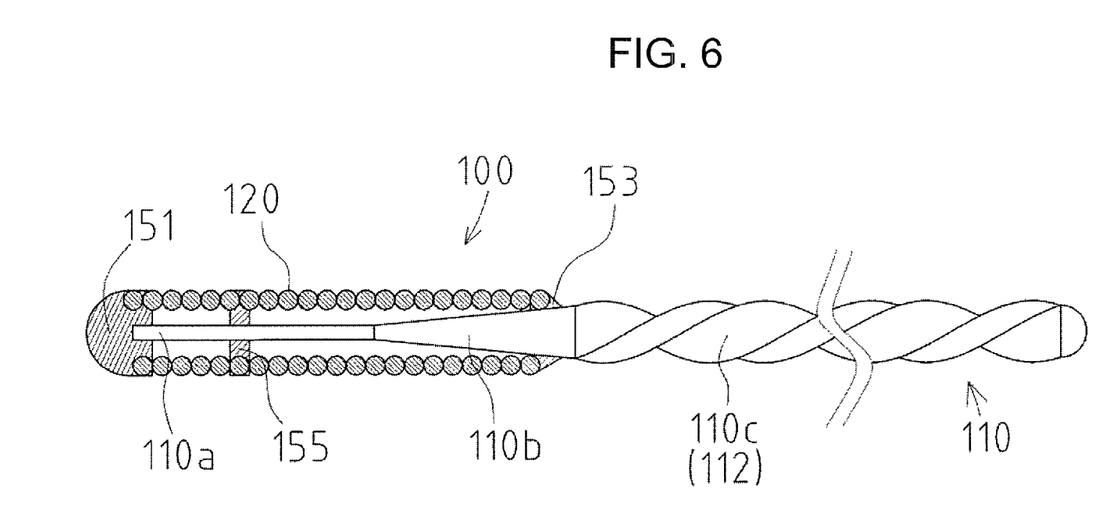
FIG. 6 is a general view showing an exemplary embodiment of a guidewire.

FIG. 6 is a general view showing an exemplary embodiment of a guidewire. In FIG. 6, a distal end of the guidewire to be inserted into the body is provided on the left, and a proximal end of the guidewire to be operated by a manipulator such as a doctor is provided on the right. Note that, in this figure, the guidewire is schematically illustrated for understanding. Thus, the dimensions shown do not necessarily reflect actual dimensions.

A guidewire 100 shown in FIG. 6 is used for treatment of the lower extremity vasculature by, for example, the Cross-Over method. The guidewire 100 includes a core shaft 110, and a coiled body 120 covering a circumference of a distal portion of the core shaft 110.

First, description will be given for the core shaft 110. The core shaft 110 includes a small diameter portion 110a, a tapered portion 110b and a large diameter portion 110c in order from the distal end to the proximal end. The small diameter portion 110a is disposed on the most distal end of the core shaft 110 and is the most flexible part of the core shaft 110. The small diameter portion 110a is formed in a tubular shape by press working. The tapered portion 110b has a cross section formed in a tapered round shape whose diameter is gradually reduced toward the distal end. Arrangements and dimensions of the small diameter portion 110a and the tapered portion 110b can be changed appropriately to obtain desired rigidity and the like. For example, the small diameter portion 110a may have a columnar shape. Further, the number of the tapered portions 110b and the angle of the tapered portion 110b may also be set appropriately as necessary.

The large diameter portion 110c is located on a proximal end of the coiled body 120, and takes on a shape similar to that of the shaft described above. That is, the proximal end of the core shaft exposed from the coiled body 120 is twisted along its longitudinal axis, and has a helically shaped portion 112. Moreover, a cross section of the helically shaped portion 112 has a recess recessed arcuately.

Thereby, compared to a configuration without any such recess (a large-diameter portion having a cross-sectional rectangular shape), an area moment of inertia of the large diameter portion 110c is lowered. Thereby, when the guidewire 100 enters along a path winding in an inverted U-shape from the lower extremity vasculature of the right leg into the lower extremity vasculature of the left leg by, for example, the Cross-Over method, a permanent set is prevented in the guidewire 100 even when it is subjected to a load caused by contact with a blood vessel wall or the like and bends excessively. Therefore, there is no possible trouble in subsequent operation, thereby making it possible to use the guidewire 100 continuously.

Note that, in the guidewire 100, the large diameter portion 110e may be configured as any of the above described shafts shown in FIGS. 1-5 to achieve the same effects.

The core shaft 110 can be formed using materials such as, but not limited to, for example, stainless steel (SUS304), a super elastic alloy such as an Ni—Ti alloy, and a piano wire.

Next, description will be given for the coiled body 120. The coiled body 120 in the present embodiment is a single thread coil composed of helically wound wires.

As shown in FIG. 6, a distal end of the coiled body 120 is fixed to a distal end of the core shaft 110 with a distal end joint 151. A proximal end of the coiled body 120 is fixed to the core shaft 110 with a proximal end joint 153. Further, an intermediate part of the coiled body 120 located distally from the proximal end joint 153 and proximally from the distal end joint 151 is fixed the core shaft 110 with an intermediate joint 155.

Materials forming the distal end joint 151, the proximal end joint 153 and the intermediate joint 155 are not especially limited, but include, for example, brazing metal such as an Sn—Pb alloy, a Pb—Ag alloy, an Sn—Ag alloy and an Au—Sn alloy.

Materials forming the coiled body 120 are not especially limited, but can include a radiopaque wire or a radiolucent wire. Materials used for a radiopaque wire are not especially limited, but can include, for example, gold, platinum, tungsten, an alloy containing these elements (for example, a platinum-nickel alloy), or the like. Moreover, materials used for a radiolucent wire are not especially limited, but can include, for example, stainless steel (SUS304, SUS316 and the like), a super elastic alloy such as an Ni—Ti alloy, a piano wire, and the like.

Figure 7:
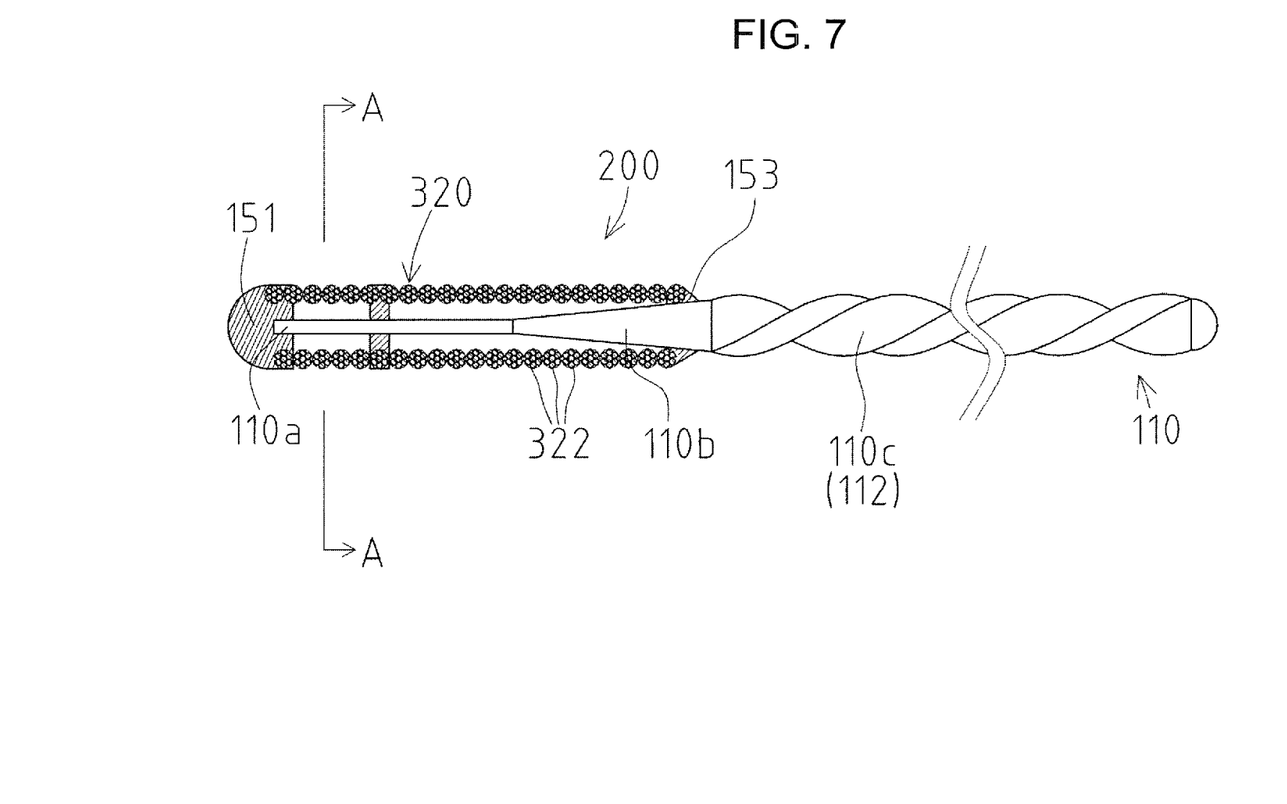
FIG. 7 is a general view showing an exemplary embodiment of a guidewire.

FIG. 7 is a general view showing a guidewire according to an exemplary embodiment. In FIG. 7, a distal end of the guidewire to be inserted into the body is provided on the left, and a proximal end of the guidewire to be operated by a manipulator such as a doctor is provided on the right. Note that, in this figure, the guidewire is schematically illustrated for understanding. Thus the dimensions shown do not necessarily reflect actual dimensions.

Figure 8:
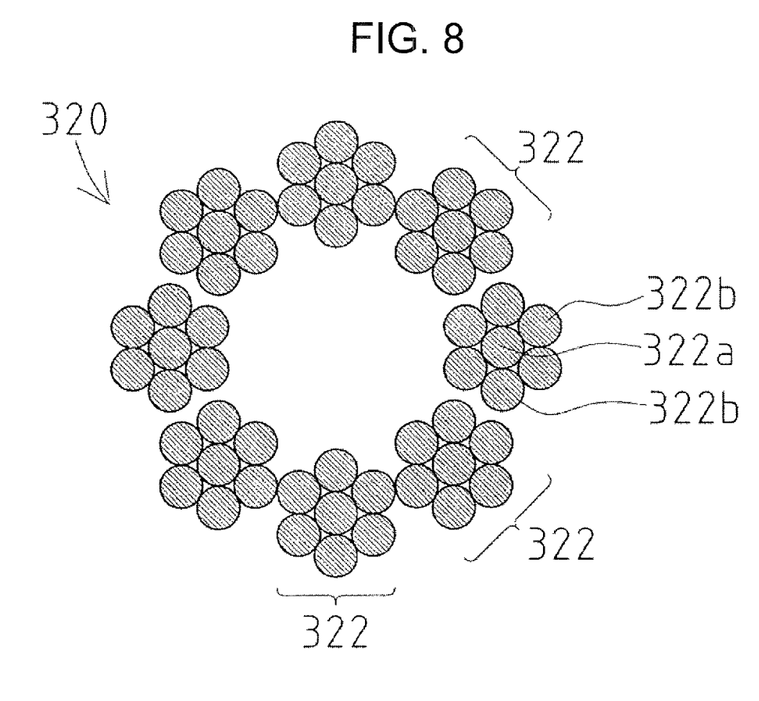
FIG. 8 is a cross-sectional view along A-A of a first coiled body in FIG. 7.

A guidewire 200 of the present embodiment has a configuration of a coiled body different from that of the guidewire 100. That is, as shown in FIG. 8, a coiled body 320 employed in the guidewire 200 of the present embodiment is composed of a plurality of helically wound strands 322 (eight strands in the present embodiment), each strand 322 being made of a core wire (wire) 322a and six side lines (wires) 322b wound so as to cover a circumference of the core wire 322a. Materials forming the core wire 322a and the side line 322b are not especially limited, but include, for example, stainless steel, tungsten, an Ni—Ti alloy and the like.

According to the guidewire 200 of the present embodiment, compared to a guidewire including a coiled body composed of, for example, a single wire having an external diameter nearly equal to that of the guidewire 200, flexibility of the coiled body is improved, thereby making it possible to secure sufficient torque transmission characteristics. Further, breaking strength against twisting is improved, so that safety of the guidewire 200 is also enhanced.

What is claimed is:

1. A shaft comprising:
a rod-like body that includes a twisted elongated shape that twists along its longitudinal axis,
wherein, a cross section of the rod-like body includes a rectangular shape and a first arcuate recess, the rectangular shape extending in a first direction perpendicular to the longitudinal axis.

2. The shaft according to claim 1, wherein the cross section of the rod-like body includes a second arcuate recess, the first arcuate recess and the second arcuate recess being disposed on a first pair of sides opposite to each other among sides forming the cross section.

3. The shaft according to claim 2, wherein the cross section of the elongated body includes a first arcuate projection and a second arcuate projection disposed on a second pair of sides of the cross section that are opposite to each other.

4. The shaft according to claim 3, wherein a radius of curvature of the first and second arcuate projections is smaller than a radius of curvature of a virtual circle having a diameter equivalent to a length of the cross section in the first direction.

5. The shaft according to claim 3, wherein a radius of curvature of the first and second arcuate projections is equal to a radius of curvature of a virtual circle having a diameter equivalent to a length of the cross section in the first direction.

6. A guidewire comprising:
a core shaft; and
a coiled body covering a distal portion of the core shaft, wherein:
the core shaft includes a proximal portion that extends proximally from a proximal end of the coiled body, the proximal portion of the core shaft including a twisted elongated body that twists along its longitudinal axis,
a cross section of the elongated body includes a rectangular shape and a first arcuate recess, the rectangular shape extending in a first direction perpendicular to the longitudinal axis.

7. The guidewire according to claim 6, wherein the cross section of the elongated body includes a second arcuate recess, the first arcuate recess and the second arcuate recess being disposed on a first pair of sides opposite to each other among sides forming the cross section.

8. The guidewire according to claim 7, wherein the cross section of the elongated body includes a first arcuate projection and a second arcuate projection on a second pair of sides of the cross section that are opposite to each other.

9. The guidewire according claim 8, wherein a radius of curvature of the first and second arcuate projections is smaller than a radius of curvature of a virtual circle having a diameter equivalent to a length of the cross section in a first direction.

10. The guidewire according claim 8, wherein a radius of curvature of the first and second arcuate projections is the same as a radius of curvature of a virtual circle having a diameter equivalent to a length of the cross section in a first direction.

11. The guidewire according to claim 6, wherein the coiled body comprises a plurality of helically wound strands, each of the strands including a plurality of wires.

\* \* \* \* \*